United States Patent
Kitagawa et al.

(10) Patent No.: US 8,940,332 B2
(45) Date of Patent: Jan. 27, 2015

(54) HIGH-MOLECULAR WEIGHT CONJUGATE OF PODOPHYLLOTOXINS

(75) Inventors: Masayuki Kitagawa, Kita-ku (JP);
Keizou Ishikawa, Kita-ku (JP);
Keiichirou Yamamoto, Kita-ku (JP);
Kazutoshi Takashio, Kita-ku (JP);
Masao Shibata, Kita-ku (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 741 days.

(21) Appl. No.: 12/226,962

(22) PCT Filed: May 16, 2007

(86) PCT No.: PCT/JP2007/060026
§ 371 (c)(1),
(2), (4) Date: Dec. 31, 2008

(87) PCT Pub. No.: WO2007/135910
PCT Pub. Date: Nov. 29, 2007

(65) Prior Publication Data
US 2009/0162313 A1    Jun. 25, 2009

(30) Foreign Application Priority Data
May 18, 2006  (JP) .................................. 2006-138509

(51) Int. Cl.
*A61K 9/14*        (2006.01)
*A61K 31/7048*  (2006.01)
(Continued)

(52) U.S. Cl.
CPC ........... *A61K 31/7048* (2013.01); *A61K 9/0019* (2013.01); *A61K 31/365* (2013.01);
(Continued)

(58) Field of Classification Search
CPC .................... A61K 31/365; A61K 31/7048
USPC ......................................................... 424/486
See application file for complete search history.

(56) References Cited

U.S. PATENT DOCUMENTS

| 3,979,449 A | 9/1976 | Hirsbrunner et al. |
| 4,734,512 A | 3/1988 | Kaneko et al. ................ 549/214 |

(Continued)

FOREIGN PATENT DOCUMENTS

| CA | 2 383 240 A1 | 3/2001 |
| CA | 2 334 615 A1 | 8/2001 |

(Continued)

OTHER PUBLICATIONS

Chinese Office Action dated Nov. 10, 2010 in co-pending U.S. Appl. No. 12/309,061, filed Mar. 3, 2009/Foreign Application No. 200780027210.8.

(Continued)

*Primary Examiner* — Benjamin Packard
(74) *Attorney, Agent, or Firm* — Nields, Lemack & Frame, LLC

(57) ABSTRACT

A novel podophyllotoxin derivative, which is capable of releasing a drug without depending on biological enzymes and can be expected to have an effective therapeutic effect and is soluble in water has been demanded. A polymer having a polyethyleneglycol structural unit and two or more succinic monoamide structural units, particularly a polymer conjugate of a podophyllotoxin in which a carboxylic acid group of polyethyleneglycol/polyaspartic acid copolymer and a hydroxyl group of podophyllotoxin and linked via an ester bond is provided.

5 Claims, 1 Drawing Sheet

(51) Int. Cl.

| | | |
|---|---|---|
| *A61K 9/00* | (2006.01) | |
| *A61K 31/365* | (2006.01) | |
| *A61K 47/48* | (2006.01) | |
| *C08G 65/331* | (2006.01) | |
| *C08G 65/332* | (2006.01) | |
| *C08G 73/10* | (2006.01) | |
| *C08G 83/00* | (2006.01) | |
| *C08L 71/02* | (2006.01) | |
| *A61K 47/26* | (2006.01) | |
| *C08L 77/00* | (2006.01) | |

(52) U.S. Cl.
CPC ........ *A61K47/48215* (2013.01); *C08G 65/331* (2013.01); *C08G 65/3314* (2013.01); *C08G 65/3324* (2013.01); *C08G 73/1092* (2013.01); *C08G 83/00* (2013.01); *C08L 71/02* (2013.01); *A61K 47/26* (2013.01); *C08L 77/00* (2013.01); *C08L 2203/02* (2013.01); *C08L 2205/05* (2013.01)
USPC ......................................................... 424/486

(56) References Cited

U.S. PATENT DOCUMENTS

| | | | |
|---|---|---|---|
| 4,892,733 | A | 1/1990 | Bichon et al. |
| 5,037,883 | A | 8/1991 | Kopecek et al. |
| 5,182,203 | A | 1/1993 | Ebersole et al. |
| 5,412,072 | A | 5/1995 | Sakurai et al. |
| 5,438,072 | A | 8/1995 | Bobee et al. |
| 5,510,103 | A | 4/1996 | Yokoyama et al. |
| 5,552,517 | A | 9/1996 | Martin |
| 5,571,889 | A | 11/1996 | Katoh et al. |
| 5,614,549 | A | 3/1997 | Greenwald et al. ............ 514/449 |
| 5,639,832 | A | 6/1997 | Kroner et al. |
| 5,693,751 | A | 12/1997 | Sakurai et al. |
| 5,877,205 | A | 3/1999 | Andersson |
| 5,985,548 | A | 11/1999 | Collier et al. |
| 6,025,385 | A | 2/2000 | Shimizu et al. |
| 6,153,655 | A | 11/2000 | Martinez et al. |
| 6,262,107 | B1 | 7/2001 | Li et al. |
| 6,322,817 | B1 | 11/2001 | Maitra et al. |
| 6,376,470 | B1 | 4/2002 | Greenwald et al. |
| 6,410,731 | B2 | 6/2002 | Curran et al. |
| 6,458,347 | B1 | 10/2002 | Sugawara et al. |
| 6,573,284 | B1 | 6/2003 | Riley et al. |
| 6,596,757 | B1 | 7/2003 | Chari et al. |
| 6,713,454 | B1 | 3/2004 | Ekwuribe et al. ................ 514/25 |
| 6,720,304 | B1 | 4/2004 | Sinn et al. |
| 6,720,306 | B2 | 4/2004 | Greenwald et al. |
| 6,858,582 | B2 | 2/2005 | Yatvin et al. |
| 7,138,490 | B2 | 11/2006 | Nakanishi et al. |
| 7,176,185 | B2 | 2/2007 | Hilfinger et al. |
| 7,495,099 | B2 | 2/2009 | Kitagawa et al. |
| 7,700,709 | B2 | 4/2010 | Masuda et al. |
| 7,820,759 | B2 | 10/2010 | Shimizu et al. |
| 8,188,222 | B2 | 5/2012 | Yamamoto et al. |
| 8,323,669 | B2 | 12/2012 | Kitagawa et al. |
| 8,334,364 | B2 | 12/2012 | Yamamoto et al. |
| 8,703,878 | B2 | 4/2014 | Kitagawa et al. |
| 8,808,749 | B2 | 8/2014 | Kitagawa et al. |
| 2001/0003779 | A1 | 6/2001 | Curran et al. |
| 2001/0014354 | A1 | 8/2001 | Yokoyama et al. |
| 2001/0041189 | A1 | 11/2001 | Xu ............................... 424/488 |
| 2002/0009426 | A1 | 1/2002 | Greenwald et al. |
| 2002/0016285 | A1 | 2/2002 | Bhatt et al. |
| 2002/0099013 | A1 | 7/2002 | Piccariello et al. |
| 2002/0119951 | A1 | 8/2002 | Seyedi et al. |
| 2002/0161062 | A1 | 10/2002 | Biermann et al. |
| 2002/0183259 | A1 | 12/2002 | Choe et al. |
| 2003/0032593 | A1 | 2/2003 | Wender et al. |
| 2003/0054977 | A1 | 3/2003 | Kumar et al. |
| 2003/0149003 | A1 | 8/2003 | Chaplin et al. |
| 2005/0054026 | A1 | 3/2005 | Atsushi et al. |
| 2005/0119193 | A1 | 6/2005 | Motoyama |
| 2005/0147617 | A1 | 7/2005 | Ji et al. |
| 2005/0171036 | A1 | 8/2005 | Arakawa et al. |
| 2006/0009622 | A1 | 1/2006 | Fuselier et al. |
| 2006/0057219 | A1 | 3/2006 | Nagasaki et al. |
| 2006/0067910 | A1 | 3/2006 | Kitagawa et al. |
| 2006/0099265 | A1 | 5/2006 | Shimizu et al. |
| 2006/0233883 | A1 | 10/2006 | Ishihara et al. |
| 2006/0258569 | A1 | 11/2006 | McTavish |
| 2007/0004674 | A1 | 1/2007 | Shiotsu et al. |
| 2007/0196497 | A1 | 8/2007 | Pouliquen et al. |
| 2008/0113028 | A1 | 5/2008 | Shimizu et al. |
| 2008/0145432 | A1 | 6/2008 | Kakizawa et al. |
| 2008/0221062 | A1 | 9/2008 | Miyamoto et al. |
| 2008/0269218 | A1 | 10/2008 | Kuramochi et al. |
| 2008/0280937 | A1 | 11/2008 | Leamon et al. |
| 2009/0012252 | A1 | 1/2009 | Masuda et al. |
| 2009/0156742 | A1 | 6/2009 | Shimizu et al. |
| 2009/0162313 | A1 | 6/2009 | Kitagawa et al. |
| 2009/0239782 | A1 | 9/2009 | Nakamura et al. |
| 2009/0275732 | A1 | 11/2009 | Hirotsu et al. |
| 2009/0281300 | A1 | 11/2009 | Yamamoto et al. |
| 2010/0004403 | A1 | 1/2010 | Kitagawa et al. |
| 2010/0029849 | A1 | 2/2010 | Yamamoto et al. |
| 2010/0234537 | A1 | 9/2010 | Kitagawa et al. |
| 2010/0292414 | A1 | 11/2010 | Kitagawa et al. |
| 2011/0136990 | A1 | 6/2011 | Harada et al. |
| 2011/0201754 | A1 | 8/2011 | Kitagawa |
| 2011/0294980 | A1 | 12/2011 | Nakanishi |
| 2012/0116051 | A1 | 5/2012 | Kitagawa et al. |
| 2013/0331517 | A1 | 12/2013 | Yamamoto et al. |
| 2014/0024703 | A1 | 1/2014 | Shimizu et al. |
| 2014/0142167 | A1 | 5/2014 | Shimizu et al. |

FOREIGN PATENT DOCUMENTS

| | | |
|---|---|---|
| CN | 1307866 | 8/2001 |
| CN | 1708540 | 12/2005 |
| CN | 1800238 | 7/2006 |
| EP | 0 397 307 A2 | 11/1990 |
| EP | 0 583 955 A2 | 2/1994 |
| EP | 0 757 049 A1 | 2/1997 |
| EP | 1 127 570 A2 | 8/2001 |
| EP | 1580216 A1 | 9/2005 |
| EP | 1 857 446 A1 | 11/2007 |
| JP | 61-243026 A | 10/1986 |
| JP | 62-96088 | 5/1987 |
| JP | 62-96088 A | 5/1987 |
| JP | 62-145093 | 6/1987 |
| JP | 63-10789 | 1/1988 |
| JP | 63-10789 A | 1/1988 |
| JP | 63-23884 | 2/1988 |
| JP | 63-23884 A | 2/1988 |
| JP | 63-502037 A | 8/1988 |
| JP | 64-61422 | 3/1989 |
| JP | 64-61423 | 3/1989 |
| JP | 2-300133 A | 12/1990 |
| JP | 5-955 A | 1/1993 |
| JP | 5-117385 A | 5/1993 |
| JP | 6-107565 A | 4/1994 |
| JP | 6-206815 A | 7/1994 |
| JP | 6-206830 A | 7/1994 |
| JP | 6-206832 A | 7/1994 |
| JP | 6-329085 A | 11/1994 |
| JP | 8-48766 | 2/1996 |
| JP | 8-503689 A | 4/1996 |
| JP | 8-507558 A | 8/1996 |
| JP | 8-310970 A | 11/1996 |
| JP | 2694923 | 9/1997 |
| JP | 10-513187 | 12/1998 |
| JP | 11-335267 A | 12/1999 |
| JP | 2000-515132 A | 11/2000 |
| JP | 2000-516948 A | 12/2000 |
| JP | 2000-517304 A | 12/2000 |
| JP | 2001-226294 A | 8/2001 |
| JP | 3268913 | 1/2002 |
| JP | 2002-69184 A | 3/2002 |
| JP | 2002-508400 A | 3/2002 |
| JP | 2002-512265 A | 4/2002 |

(56) References Cited

FOREIGN PATENT DOCUMENTS

| | | | |
|---|---|---|---|
| JP | 3310000 A | 5/2002 |
| JP | 2003-509385 | 3/2003 |
| JP | 2003-509386 A | 3/2003 |
| JP | 2003-511349 | 3/2003 |
| JP | 2003-511423 A | 3/2003 |
| JP | 2003-524028 A | 8/2003 |
| JP | 2003-525238 | 8/2003 |
| JP | 2003-527443 A | 9/2003 |
| JP | 2003-342167 A | 12/2003 |
| JP | 2003-342168 A | 12/2003 |
| JP | 2003-342269 A | 12/2003 |
| JP | 2004-530736 A | 10/2004 |
| JP | 2004-532289 A | 10/2004 |
| JP | 2005-51922 A | 2/2005 |
| JP | 2005-507912 A | 3/2005 |
| JP | 2005-508832 A | 4/2005 |
| JP | 2005-517675 A | 6/2005 |
| JP | 2005-519122 A | 6/2005 |
| JP | 2005-533026 A | 11/2005 |
| JP | 2006-510627 A | 3/2006 |
| JP | 2006-511571 A | 4/2006 |
| JP | 2006-120914 A | 5/2006 |
| JP | 2006-517572 A | 7/2006 |
| JP | 2006-521367 A | 9/2006 |
| JP | 2006-524673 A | 11/2006 |
| JP | 2007-111211 A | 5/2007 |
| JP | 2007-511586 A | 5/2007 |
| JP | 2007-191643 A | 8/2007 |
| JP | 2008-41610 A | 2/2008 |
| WO | 93/24476 A | 12/1993 |
| WO | 96/23794 A | 8/1996 |
| WO | 97/38727 A | 10/1997 |
| WO | 98/02426 A | 1/1998 |
| WO | 98/07713 A | 2/1998 |
| WO | 98/08489 A1 | 3/1998 |
| WO | 99/30727 A1 | 6/1999 |
| WO | 99/53951 A | 10/1999 |
| WO | 01/19361 A2 | 3/2001 |
| WO | 01/19406 | 3/2001 |
| WO | 01/19407 A2 | 3/2001 |
| WO | 01/26693 A2 | 4/2001 |
| WO | 01/64198 A2 | 9/2001 |
| WO | 01/70275 A2 | 9/2001 |
| WO | 01/92584 A1 | 12/2001 |
| WO | 02/06279 A1 | 1/2002 |
| WO | 02/065986 A2 | 8/2002 |
| WO | 02/065988 A2 | 8/2002 |
| WO | 02/066066 A1 | 8/2002 |
| WO | 03/000771 A1 | 1/2003 |
| WO | 03/035008 A2 | 5/2003 |
| WO | 03/055860 A1 | 7/2003 |
| WO | 2004/039869 | 5/2004 |
| WO | 2004/039869 A1 | 5/2004 |
| WO | 2004/050087 A1 | 6/2004 |
| WO | 2004/056782 A1 | 7/2004 |
| WO | 2004/072051 A1 | 8/2004 |
| WO | 2004/082718 A1 | 9/2004 |
| WO | 2004/096212 A1 | 11/2004 |
| WO | 2005/000300 A1 | 1/2005 |
| WO | 2005/018674 A1 | 3/2005 |
| WO | 2005/066214 A1 | 7/2005 |
| WO | 2006/033296 A1 | 3/2006 |
| WO | 2006/055670 A2 | 5/2006 |
| WO | 2006/055760 A1 | 5/2006 |
| WO | 2006/095668 A1 | 9/2006 |
| WO | 2006/095783 A1 | 9/2006 |
| WO | 2006/101052 A1 | 9/2006 |
| WO | 2006/115293 A1 | 11/2006 |
| WO | 2006/120914 A | 11/2006 |
| WO | 2006/120915 A1 | 11/2006 |
| WO | 2007/022493 A2 | 2/2007 |
| WO | 2007/080898 A1 | 7/2007 |
| WO | 2007/111211 A1 | 10/2007 |
| WO | 2007/135910 A1 | 11/2007 |
| WO | 2008/010463 A1 | 1/2008 |
| WO | 2008/041610 A1 | 4/2008 |
| WO | 2008/056596 A1 | 5/2008 |
| WO | 2008/056654 A1 | 5/2008 |
| WO | 2009/041570 A1 | 4/2009 |
| WO | 2009/116509 A1 | 9/2009 |
| WO | 2009/142326 A1 | 11/2009 |
| WO | 2010/131675 A1 | 11/2010 |

OTHER PUBLICATIONS

Korean Office Action dated Nov. 8, 2010 in co-pending U.S. Appl. No. 10/548,998, filed Oct. 31, 2005/Foreign Application No. 10-2005-7017245.
Final Rejection dated Jun. 8, 2011 in co-pending U.S. Appl. No. 11/662,834.
Office Action dated Jun. 16, 2011 in co-pending U.S. Appl. No. 12/225,230.
Final Rejection dated Jul. 27, 2011 in co-pending U.S. Appl. No. 12/311,086.
Russian Communication, with English translation, dated May 16, 2011 in corresponding foreign patent application No. RU 2008149932/04.
The European communication dated Oct. 23, 2009.
International Search Report dated Aug. 21, 2007.
Advanced Drug Delivery Reviews 20 (1996) 1995-201: K. Yokoyama et al; "Limethason as a lipid microsphere preparation: An overview".
International Search Report dated Jan. 29, 2008 in co-pending U.S. Appl. No. 12/312,009 (PCT/JP2007/071305).
International Search Report dated Jan. 29, 2008 in co-pending U.S. Appl. No. 12/312,157 (PCT/JP200/071532).
Chinese communication dated Aug. 11, 2010 in a corresponding foreign application (CN2007800177809).
International Search Report dated Dec. 24, 2003 in U.S. patent 7,495,099.
Taiwanese communication dated Nov. 30, 2006 in U.S. patent 7,495,099.
Russian communication dated Apr. 20 2007 in U.S. patent 7,495,099.
European communication dated Sep. 25, 2008 in U.S. patent 7,495,099.
International Search Report dated May 11, 2004 in co-pending U.S. Appl. No. 10/548,998.
Chinese communication dated Oct. 20, 2006 in co-pending U.S. Appl. No. 10/548,998.
Russian communication dated Jun. 27, 2007 in co-pending U.S. Appl. No. 10/548,998.
European communication dated Feb. 17, 2009 in co-pending U.S. Appl. No. 10/548,998.
Chinese communication dated Apr. 17, 2009 in co-pending U.S. Appl. No. 10/548,998.
European communication dated Jun. 5, 2009 in co-pending U.S. Appl. No. 10/548,998.
International Search Report dated Nov. 15, 2005 in co-pending U.S. Appl. No. 12/322,322.
International Search Report dated Jul. 25, 2006 in U.S. Appl. No. 7,700,709.
International Search Report dated May 15, 2007 in co-pending U.S. Appl. No. 12/225,230.
International Search Report dated Oct. 16, 2007 in co-pending U.S. Appl. No. 12/309,061.
International Search Report dated Jan. 8, 2008 in co-pending U.S. Appl. No. 12/311,086.
International Search Report dated Jan. 29, 2008 in co-pending U.S. Appl. No. 12/312,009.
Office Actions dated Jan. 21, 2009, Apr. 17, 2009, Jul. 10, 2009, Mar. 4, 2010 in co-pending U.S. Appl. No. 10/548,998.
Office Actions dated Oct. 19, 2009, Mar. 19, 2010, Jun. 23, 2010, Jul. 7, 2010 in co-pending application 12/322,322.
Office Action dated Aug. 24, 2010 in co-pending U.S. Appl. No. 11/662,834.
Office Actions dated Jul. 21, 2010 in co-pending U.S. Appl. No. 12/309,061.

(56) References Cited

OTHER PUBLICATIONS

A.V. Shur, "High-Molecular Weight Compounds"; Course for Universities, Third Edition, Revised and supplemented, "Visshaja Shkola" Publishing House, 1981, 656 pages, see p. 265).
Chemical Abstracts, 6001, vol. 132; Oct. 10, 2000 No. 2—XP-002168038.
Merriam-Webster's Collegiate Dictionary—Eleventh Edition 2004.
J. Org. Chem. 2001, 66, 8135-8138; Keirs Gaukroger, et al.; "Novel Synthesis of Cis and Trans Isomers of Combretastatin A-4".
Anti-Cancer Drug Design; vol. 14, No. 6, Dec. 1999—ISSN 0266-9536.
Journal of Pharmaceutical Sciences, vol. 92, No. 7, Jul. 2003; Monica L. Adams et al.; "MiniReview—Amphiphilic Block Copolymers for Drug Delivery".
Chemistry and Biology, vol. 11, 787-797, Jun. 2004; Maria Vilenchick et al.; "Targeting Wide-Range Oncogenic Transformation via PU24FCI, a specific Inhibitor of Tumor Hsp90".
Trends in Molecular Medicine vol. 8, No. 4 (Suppl.) 2002; Len Neckers; "Hsp90 inhibitors as novel cancer chemotherapeutic agents".
Current Cancer Drug Targets, 2003, 3, 385-390; Udai Banerji et al.; "The Clinical Applications of Heat Shock Protein Inhibitors in Cancer Present and Future".
Cancer Sci; Feb. 2004; vol. 95; No. 2; 105-111; Akira Matsuda et al.; "Antitumor Activity of Sugar-Modified Cytosine Nucleosides".
Cancer Research 44, Jan. 25-30, 1984; Yoshinori Kato et al.; "Antitumor Activity of 1-B-D-Arabinofuranosylcytosine Conjugated with Polyglutamic Acid and Its Derivative".
Journal of Controlled Release 79 (2002) 55-70; Yun H. Choe et al.; "Anticancer Drug Delivery Systems: Multi-Loaded N4-acyl poly-(ethylene glycol) prodrugs of ara-C. II. Efficacy in ascites and solid tumors".
Journal of Pharmacokinetics and Biopharmaceutics, vol. 23, No. 4, 1995; Claudia S. Leopold; In vivo Pharmacokinetic Study for the Assessment of Poly(L-Aspartic Acid) as a Drug Carrier for Colon-Specific Drug Delivery).
International Search Report dated Dec. 9, 2008 in co-pending U.S. Appl. No. 12/678,620.
Bioorganic & Medicinal Chemistry Letters 15 (2005) pp. 3338-3343, "The identification, synthesis, protein crystal structure and in vitro biochemical evaluation of a new 3,4-diarylpyrazole class of Hsp90 inhibitors", Cheung, et al.
Molecular Cancer Therapeutics, 2006, 5(6), Jun. 2006, pp. 1628-1637, "Preclinical pharmacokinetics and metabolism of a novel diary pyrazole resorcinol series of heat shock protein 90 inhibitors", Smith, et al.
Registry Entry for Registry No. 171009-07-7, which entered STN on Dec. 6, 1995, 3 pages.
Registry Entry for Registry No. 7689-03-4, which entered STN on Nov. 16, 1984, 3 pages.
Merriam-Webster Online Dictionary entry for "Derivative", (http://www.merriam-webstercom/dictionary/derivative), last accessed Feb. 9, 2011, 3 pages.
Office Action dated Apr. 4, 2011 in co-pending U.S. Appl. No. 12/311,086.
Final Rejection dated Feb. 28, 2011 in co-pending U.S. Appl. No. 12/309,061.
Office Action Nov. 12, 2010 in a co-pending U.S. Appl. No. 11/662,834.
Journal of Peptide Science, vol. 3, 141-144 (1997); Jan Izdebski et al.; "Evaluation of Carbodiimides Using a Competition Method".
European Communication, dated Oct. 28, 2011 in co-pending European Patent Application No. EP 05783310.5.
Australian Communication, dated Oct. 28, 2011 in corresponding Australian Patent Application No. 2007252678.
Office Action dated Oct. 12, 2011 in co-pending U.S. Appl. No. 12/312,157.
Office Action mailed Oct. 25, 2011 in co-pending U.S. Appl. No. 12/312,009.
Final Rejection mailed Nov. 8, 2011 in co-pending U.S. Appl. No. 12/225,230.
Chinese Communication, with English translation, dated Sep. 23, 2011 in corresponding Chinese patent application No. 2007800177809.
Journal of Controlled Release, 2001, V. 74, No. 1-3, pp. 295-302, paragraph of "2. Structure of NK911", "Development of the polymer micelle carrier system for doxorubicin", Nakanishi, et al.
International Search Report mailed Jun. 23, 2009 in co-pending PCT application No. PCT/JP2009/055115.
Chinese Communication, with English translation, dated Aug. 31, 2011 in co-pending Chinese patent application No. 200980110087.5.
Chinese Communication, with English translation, dated Oct. 10, 2011 in co-pending Chinese Patent Application No. 200880109404.7.
Office Action dated Dec. 15, 2011 in co-pending U.S. Appl. No. 11/662,834.
Colloids and Surfaces B: Biointerfaces V. 16 (1999) pp. 217-226, "Micelle-like structures of poly(ethyleneoxide)-block-poly(2-hydroxyethyl aspartamide)-methotrexate conjugates", Li, et al.
Pharmaceutical Research, V. 17, No. 5 (2000), pp. 607-611, "Methotrexate Esters of Poly (EthyleneOxide)-Block-Poly (2-Hydroxyethyl-L-Aspartamide). Part I: Effects of the Level of Methotrexate Conjugation on the Stability of Micelles and on Drug Release", Li, et al.
International Search Report dated Jul. 21, 2009 in co-pending international patent application No. PCT/JP2009/058325.
Taiwan Communication, with English translation, dated Jul. 22, 2011 in co-pending Taiwan Patent Application No. 094132581.
Final Rejection mailed Mar. 5, 2013 in co-pending U.S. Appl. No. 12/922,747.
Advanced Drug Delivery Reviews, vol. 55, No. 2, Feb. 2003, pp. 217-250, "Effective drug delivery by PEGylated drug conjugates", Greenwald, et al.
European Communication mailed May 24, 2013 in co-pending European patent application No. 09722008.1.
Office Action mailed Jun. 12, 2013 in co-pending U.S. Appl. No. 13/319,175.
International Search Report and Written Opinion mailed Jan. 24, 2012 in co-pending PCT application No. PCT/JP2011/076373.
Japanese Communication, with partial English translation, mailed May 14, 2013 in co-pending Japanese patent application No. JP 2009-534401.
International Search Report mailed Dec. 4, 2012 in co-pending PCT application No. PCT/JP2012/072160.
Written Opinion mailed Dec. 4, 2012 in co-pending PCT application No. PCT/JP2012/072160.
International Preliminary Report on Patentability mailed Mar. 20, 2014 in co-pending PCT application No. PCT/JP2012/072160.
Final Rejection mailed Apr. 7, 2014 in co-pending U.S. Appl. No. 12/922,747.
Japanese Communication, with English translation, mailed Mar. 26, 2013 in co-pending Japanese Patent Application No. 2008-537500.
Japanese communication, with English translation, mailed Sep. 24, 2013 in co-pending Japanese patent application No. JP 2010-503871.
Office Action mailed Oct. 7, 2013 in co-pending U.S. Appl. No. 10/548,998.
Notice of Allowance mailed May 15, 2014 in co-pending U.S. Appl. No. 13/319,175.
Canadian Communication issued Jun. 26, 2013 in co-pending Canadian patent application No. CA 2,664,852.
International Preliminary Report on Patentability, with English translation, issued Apr. 7, 2009 and Apr. 22, 2009 in co-pending PCT application No. PCT/JP2007/068841.
Final Rejection mailed Aug. 28, 2013 in co-pending U.S. Appl. No. 12/311,086.
Office Action mailed Sep. 6, 2013 in co-pending U.S. Appl. No. 12/922,747.
The Merck Index, Fourteenth Edition, 2006, p. 1-16, O'Neil, et al.
Chinese Communication, with English translation, mailed Feb. 22, 2013 in co-pending Chinese Patent Application No. 201080021960.6.

(56) References Cited

OTHER PUBLICATIONS

Office Action mailed Apr. 18, 2013 in co-pending U.S. Appl. No. 12/311,086.
Final Rejection mailed Jan. 10, 2014 in co-pending U.S. Appl. No. 13/319,175.
Notice of Allowance mailed Jan. 16, 2014 in co-pending U.S. Appl. No. 12/678,620.
Final Rejection mailed Aug. 21, 2012 in co-pending U.S. Appl. No. 11/662,834.
Notice of Allowance mailed Aug. 28, 2012 in co-pending U.S. Appl. No. 12/225,230.
Notice of Allowance mailed Aug. 7, 2012 in co-pending U.S. Appl. No. 12/312,009.
Office Action mailed Jul. 30, 2012 in co-pending U.S. Appl. No. 12/922,747.
Office Action—Restriction—mailed Jul. 11, 2012 in co-pending U.S. Appl. No. 12/991,041.
Office Action mailed Aug. 22, 2012 in co-pending U.S. Appl. No. 12/991,041.
Office Action—Restriction—mailed Jan. 29, 2013 in co-pending U.S. Appl. No. 13/319,175.
Taiwanese Communication, with English translation, dated Dec. 14, 2011 in co-pending Taiwanese Application No. 094132581.
Office Action Feb. 21, 2012 in co-pending U.S. Appl. No. 12/312,009.
Notice of Allowance dated Mar. 1, 2012 in co-pending U.S. Appl. No. 12/312,157.
Chinese Communication, with English translation, mailed Dec. 31, 2013 in co-pending Chinese patent application No. CN 200980110087.5.
European Communication mailed Jan. 27, 2012 in co-pending European Patent Application No. 07831039.8.
Antimicrobial Agents and Chemotherapy, vol. 2, No. 5, Nov. 1972, pp. 395-401, XP 55016709, ISSN: 0066-4804, "Antiviral Action of Camptothecin", Horwitz, et al.
International Search Report mailed Aug. 10, 2010 in co-pending PCT Application No. PCT/JP2010/058034.
Office Action mailed Apr. 6, 2012 in co-pending U.S. Appl. No. 12/225,230.
Miscellaneous Communication mailed Mar. 19, 2012 in co-pending U.S. Appl. No. 12/312,157.
Office Action mailed Apr. 25, 2012 in co-pending U.S. Appl. No. 12/678,620.
Office Action-Restriction-mailed Apr. 27, 2012 in co-pending U.S. Appl. No. 12/922,747.
Final Rejection mailed Oct. 17, 2012 in co-pending U.S. Appl. No. 12/678,620.
Final Rejection mailed Mar. 28, 2013 in co-pending U.S. Appl. No. 12/991,041.
Chinese communication, with English translation, mailed Jun. 17, 2014 in co-pending Chinese patent application No. 200980110087.5.
Office Action mailed Aug. 25, 2014 in co-pending U.S. Appl. No. 11/662,834.
Notice of Allowance mailed Sep. 11, 2014 in co-pending U.S. Appl. No. 12/226,962.
Examiner's Answer to Appeal Brief mailed Jul. 29, 2014 in co-pending U.S. Appl. No. 12/311,086.
Office Action mailed Oct. 1, 2014 in co-pending U.S. Appl. No. 14/241,924.
Notice of Allowance mailed Oct. 8, 2014 in co-pending U.S. Appl. No. 12/922,747.
European communication dated Oct. 29, 2014 in co-pending European patent application No. 09742696.9.
Office Action mailed Nov. 24, 2014 in co-pending U.S. Appl. No. 14/497,703.

US 8,940,332 B2

HIGH-MOLECULAR WEIGHT CONJUGATE OF PODOPHYLLOTOXINS

TECHNICAL FIELD

The present invention relates to a high-molecular weight conjugate of podophyllotoxins in which a carboxylic acid group of a polymer having a polyethylene glycol moiety and two or more succinic acid monoamide moieties is ester-bonded to a hydroxyl group of the podophyllotoxins, a method for manufacturing the same, and the use thereof.

BACKGROUND ART

Podophyllotoxin is a physiologically active substance contained in the aqueous extract of roots and stems of American Mayapple, which is a perennial plant of genus *Podophyllum*, and podophyllotoxin and derivatives thereof are known to have anticancer activity. However, many of these compounds are poorly water-soluble, and thus research on water-soluble high-molecular weight derivatives of podophyllotoxins and the like has been carried out for the purpose of further improving the effectiveness.

For example, Patent Document 1 describes a high-molecular weight derivative of podophyllotoxins conjugated to polyethylene glycol. However, in these high-molecular weight derivatives of podophyllotoxins, only one to two podophyllotoxin molecules can be bound to one molecule of polyethylene glycol because of its structure, and therefore a large quantities of polymer is required in order to administer an effective amount of the drug.

Patent Document 2 describes a molecule in which a drug is bound to a block copolymer of polyethylene glycol and polyaspartic acid, which forms micelles and has water-solubility. Patent Document 3 describes a polymeric carrier in which a hydrophobic substance is bound to a carboxylic acid group in a side chain of a block copolymer of polyethylene glycol and a poly(acidic amino acid), and which functions as a polymeric drug carrier. Patent Document 4 describes a high-molecular weight derivative of camptothecin in which a carboxylic acid group in a side chain of a block copolymer of polyethylene glycol and polyglutamic acid is bound to a phenolic hydroxyl group of the camptothecins. However, Patent Documents 2 to 4 do not describe about conjugates of podophyllotoxins.

[Patent Document 1] Japanese Patent Application Laid-Open (KOHYO) No. 10-513187

[Patent Document 2] Japanese Patent No. 2694923

[Patent Document 3] Japanese Patent No. 3268913

[Patent Document 4] International Patent Application Publication No. WO 2004/39869 Pamphlet

DISCLOSURE OF THE INVENTION

Problems to be Solved by the Invention

A bond between a polyethylene glycol moiety and a drug as described in Patent Document 1 is cleavable by hydrolyzing enzymes in the body, by which the delivery and release of the drug can be controlled. However, the hydrolyzing enzymes in the body are believed to vary widely among different species as well as among individuals within the same species. Therefore, there is a concern that the effect of the released drug would be greatly different among individuals when the cleavage of the bond to drug depends on the hydrolyzing enzymes.

In the case of the adriamycin conjugate described in Patent Document 2 in which a block copolymer is bound to adriamycin via an amide bond, the efficacy is questionable since the release of the drug by hydrolysis is slow due to the amide bond, a chemically stable bonding form.

Podophyllotoxins such as etoposide and teniposide are useful anticancer agents, and thus there is a demand for novel derivatives which are water-soluble and have excellent anticancer activity.

Means for Solving the Problems

As a result of intensive studies for solving the problems described above, the present inventors have found a phenomenon that, when a compound having a hydroxyl group is ester-bonded to a free carboxylic acid of succinic acid monoamide, the compound having the hydroxyl group is easily released as the structure of succinic acid monoamide changes to a cyclized structure (succinic acid imide). On the basis of this, the present inventors produced a high-molecular weight conjugate of podophyllotoxins in which a polymer having a polyethylene glycol moiety and succinic acid monoamide moieties is ester-bonded to a hydroxyl group of the podophyllotoxins, and found that the high-molecular weight conjugate thus obtained releases podophyllotoxins without depending on hydrolyzing enzymes, thereby completing the present invention.

Specifically, the present invention relates to the following (1) to (10).

(1) A high-molecular weight conjugate of podophyllotoxins, in which a carboxylic acid group of a polymer having a polyethylene glycol moiety and two or more succinic acid monoamide moieties is ester-bonded to a hydroxyl group of the podophyllotoxins.

(2) The high-molecular weight conjugate of podophyllotoxins according to (1) above, wherein the polymer having a polyethylene glycol moiety and two or more succinic acid monoamide moieties is a block copolymer.

(3) The high-molecular weight conjugate of podophyllotoxins according to (2) above, wherein the two or more succinic acid monoamide moieties constitute polyaspartic acid.

(4) The high-molecular weight conjugate of podophyllotoxins according to (3) above, represented by formula (I):

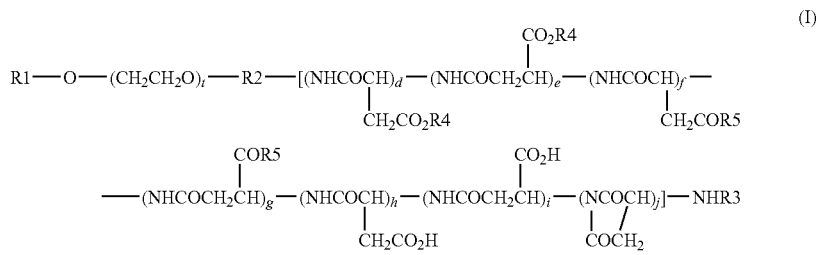

wherein R1 represents a hydrogen atom or a (C1-C6) alkyl group; R2 represents a linking group; R3 represents a hydrogen atom or a (C1-C6) acyl group; R4 represents a residue of a hydroxyl group of the podophyllotoxins; R5 represents a group selected from the group consisting of a (C1-C30) alkoxy group, a (C7-C30) aralkyloxy group, a (C1-C30) alkylamino group, a di(C1-C30) alkylamino group, an amino acid with a protected carboxyl group, and —N(R6)CONH(R7) wherein R6 and R7, which may be identical or different, each represent a (C3-C6) cyclic alkyl group or a (C1-C5) alkyl group optionally substituted with a tertiary amino group; t represents an integer from 5 to 11,500; d, e, f, g, h, i and j each independently represent an integer from 0 to 200, provided that d+e represents an integer from 1 to 200, and d+e+f+g+h+i+j represents an integer from 3 to 200, and that the respective constituent units of polyaspartic acid are bound in any order.

(5) The high-molecular weight conjugate of podophyllotoxins according to (4) above, wherein R1 is a (C1-C6) alkyl group; R2 is a (C2-C6) alkylene group; R3 is a (C1-C6) acyl group; t is an integer from 8 to 2,300; and d, e, f, g, h, i and j are each independently an integer from 0 to 100, provided that d+e is an integer from 1 to 100, and d+e+f+g+h+i+j is an integer from 6 to 100.

(6) The high-molecular weight conjugate of podophyllotoxins according to (5) above, wherein R1 is a (C1-C3) alkyl group; R2 is (C2-C4) alkylene group; R3 is a (C1-C3) acyl group; t is an integer from 100 to 300; and d, e, f, g, h, i and j are each independently an integer from 0 to 90, provided that d+e is an integer from 1 to 90, and d+e+f+g+h+i+j is an integer from 15 to 90.

(7) The high-molecular weight conjugate of podophyllotoxins according to anyone of (1) to (6) above, wherein the podophyllotoxins are podophyllotoxin, etoposide or teniposide.

(8) A high-molecular weight conjugate of podophyllotoxins, obtained by ester-bonding a carboxylic acid group of a polymer having a polyethylene glycol moiety and two or more succinic acid monoamide moieties to a hydroxyl group of the podophyllotoxins, using a dehydrating condensing agent in an organic solvent.

(9) A method for manufacturing the high-molecular weight conjugate of podophyllotoxins according to any one of (1) to (7) above, the method comprising ester-bonding a carboxylic acid group of a polymer having a polyethylene glycol moiety and two or more succinic acid monoamide moieties to a hydroxyl group of the podophyllotoxins, using a dehydrating condensing agent in an organic solvent.

(10) An anticancer agent comprising the high-molecular weight conjugate of podophyllotoxins according to any one of (1) to (8) above, as an active ingredient.

Effects of the Invention

The high-molecular weight conjugate of podophyllotoxins of the present invention is capable of releasing the drug without depending on hydrolyzing enzymes in the body, is hardly affected by individual difference, and can be expected to have efficacious therapeutic effects.

BEST MODE FOR CARRYING OUT THE INVENTION

The high-molecular weight conjugate of podophyllotoxins of the present invention is characterized in that a carboxylic acid group of a polymer having a polyethylene glycol moiety and two or more succinic acid monoamide moieties is ester-bonded to a hydroxyl group of the podophyllotoxins.

According to the present invention, the term "succinic acid monoamide moiety" means the structure —HNCO—C—C—$CO_2H$, and for instance, the examples include succinic acid monoamide (—HNCO—$CH_2$—$CH_2$—$CO_2H$), a structure in which one of the two carboxylic acid groups in aspartic acid is amidated (—HNCO—CH(—NH—)—$CH_2$—$CO_2H$ or —HNCO—$CH_2$—CH(—NH—)—$CO_2H$), and the like. These succinic acid monoamide moieties may constitute a polymer backbone, for example, as in the case of polyaspartic acid, or may be bound to functional groups of the backbone polymer composed of a polyalcohol such as dextran, a polyamine such as polylysine, or a polycarboxylic acid other than polyaspartic acid (for example, polylactic acid and the like).

Examples of the polymer having a polyethylene glycol moiety and two or more succinic acid monoamide moieties include a graft type polymer in which the polyethylene glycol moiety and the succinic monoamide moieties branch from the polymer backbone in a comb-like form, and a block-type polymer (block copolymer) in which the polymer having a polyethylene glycol moiety and succinic acid monoamide moieties are tandemly aligned, and the like.

When the two or more succinic acid monoamide moieties form polyaspartic acid, the graft-type polymer also includes a polymer in which the polyethylene glycol moiety is partially bound to the polyaspartic acid backbone, and the like, while the block-type polymer includes a polymer in which the terminal of the polyaspartic acid is bound to the terminal of the polyethylene glycol moiety, and the like.

The polyethylene glycol moiety in the polymer of the high-molecular weight conjugate of podophyllotoxins of the present invention includes polyethylene glycol in which both terminals or a single terminal is modified. When both terminals are modified, the modifying groups may be identical or different. Examples of the modifying group include a (C1-C6) alkyl group optionally having a substituent. Examples of the alkyl group of the (C1-C6) alkyl group optionally having a substituent include the following alkyl groups, and preferred is a (C1-C4) alkyl group, including, for example, a methyl group, an ethyl group, an n-propyl group, an n-butyl group, and the like. Examples of the substituent in the (C1-C6) alkyl group optionally having a substituent include, for example, an amino group, a methylamino group, a dimethylamino group, an ethylamino group, a diethylamino group, and the like.

The molecular weight of the polyethylene glycol moiety is about 300 to 500,000, preferably about 500 to 100,000, more preferably about 1000 to 50,000.

The molecular weight of the polymer having a polyethylene glycol moiety and two or more succinic acid monoamide moieties according to the present invention is about 500 to 600,000, preferably about 600 to 110,000, and more preferably about 800 to 80,000.

According to the present invention, the term "molecular weight" refers to the weight average molecular weight determined by the GPC method.

In the high-molecular weight conjugate of podophyllotoxins of the present invention, the amount of the podophyllotoxins bound to the polymer having a polyethylene glycol moiety and two or more succinic acid monoamide moieties is 1 to 100%, preferably 1 to 90%, more preferably 2 to 60%, based on the total number of carboxylic acid groups.

According to the present invention, the podophyllotoxins are not particularly limited, provided that they are the podophyllotoxins having a hydroxyl group and antitumor activity. Examples of the podophyllotoxins include podophyllotoxin represented by the following formula (II), etoposide represented by the following formula (III), teniposide represented by the following formula (IV), and the like. Examples of the hydroxyl group of the podophyllotoxins include, for example, an alcoholic hydroxyl group of the following formula (II), an alcoholic hydroxyl group on the sugar moiety or a phenolic hydroxyl group on the benzene ring of the following formula (III) or the following formula (IV), and the substituent position of the hydroxyl group is not limited.

The high-molecular weight conjugate of podophyllotoxins of the present invention may include a conjugate via either of an alcoholic hydroxyl group of podophyllotoxins or a phenolic hydroxyl group of podophyllotoxins, or a mixture thereof. Alternatively, a high-molecular weight conjugate in which podophyllotoxins bound via an alcoholic hydroxyl group and podophyllotoxins bound via a phenolic acidic group may be mixed on one molecule may also be used.

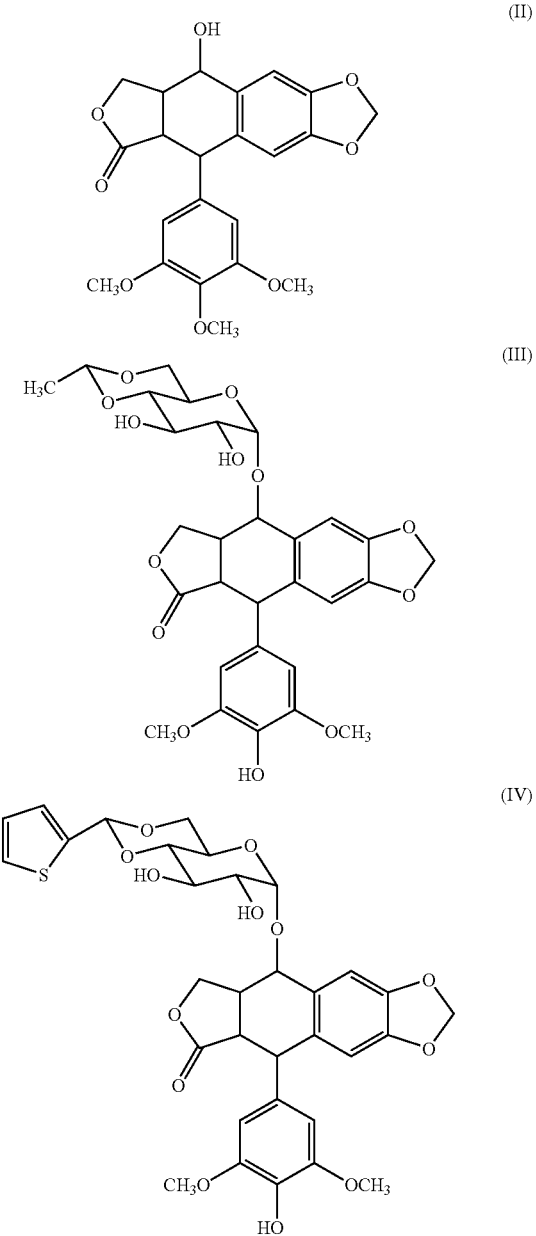

As the two or more succinic acid monoamide moieties according to the present invention, polyaspartic acid is preferred.

A preferred high-molecular weight conjugates of podophyllotoxins of the present invention includes a compound represented by the above general formula (I), wherein R1 represents a hydrogen atom or a (C1-C6) alkyl group; R2 represents a linking group; R3 represents a hydrogen atom or a (C1-C6) acyl group; R4 represents the residue of a hydroxyl group of the podophyllotoxins; R5 represents a group selected from the group consisting of a (C1-C30) alkoxy group, a (C7-C30) aralkyloxy group, a (C1-C30) alkylamino group, a di(C1-C30) alkylamino group, an amino acid with a protected carboxyl group, and —N(R6)CONH(R7) wherein R6 and R7, which may be identical or different, each represents a (C3-C6) cyclic alkyl group or a (C1-C5) alkyl group optionally substituted with a tertiary amino group; t represents an integer from 5 to 11,500; and d, e, f, g, h, i and j each independently represent an integer from 0 to 200, provided that d+e represents an integer from 1 to 200, and d+e+f+g+h+i+j represents an integer from 3 to 200, and that the respective constituent units of polyaspartic acid are bound in any order.

Examples of the (C1-C6) alkyl group for R1 in the general formula (I) include a straight-chain or branched (C1-C6) alkyl group, including for example a methyl group, an ethyl group, an n-propyl group, an i-propyl group, an n-butyl group, a t-butyl group, an n-pentyl group, an i-pentyl group, an n-hexyl group and the like, and preferred is a straight-chain or branched (C1-C4) alkyl group, and particularly preferred is a straight-chain or branched (C1-C3) alkyl group including, for example, a methyl group, an ethyl group, an n-propyl group, an i-propyl group, and more particularly preferred is a methyl group.

Examples of the linking group represented by R2 in the general formula (I) include, but are not particularly limited to, a (C2-C6) alkylene group. Preferred is a (C2-C4) alkylene group including, for example, an ethylene group, a trimethylene group, a butylene group and the like, and particularly preferred is a trimethylene group.

Examples of the (C1-C6) acyl group for R3 in the general formula (I) include, but are not particularly limited to, a formyl group, an acetyl group, a propionyl group, a pivaloyl group and the like. Preferred is a (C1-C3) acyl group, and particularly preferred is an acetyl group.

With regard to the residue of the hydroxyl group of podophyllotoxins for R4 in the general formula (I), examples of podophyllotoxins include the aforementioned podophyllotoxins, and they are not particularly limited provided that the podophyllotoxins have a hydroxyl group capable of binding to a carboxylic acid moiety of a polymer via an ester bond using a dehydrating condensing agent, and have antitumor activity. Examples of the podophyllotoxins include podophyllotoxin represented by the above formula (II), etoposide represented by the above formula (III), teniposide represented by the above formula (IV), and the like.

R5 in the general formula (I) represents a group selected from the group consisting of a (C1-C30) alkoxy group, a (C7-C30) aralkyloxy group, a (C1-C30) alkylamino group, a di(C1-C30) alkylamino group, an amino acid with a protected carboxyl group, and —N(R6)CONH(R7) wherein R6 and R7, which may be identical or different, are a (C3-C6) cycloalkyl group, or a (C1-C5) alkyl group optionally substituted with a tertiary amino group. R5 in the general formula (I) may be identical or different in one molecule, and a polymer in the high-molecular weight conjugate of podophyllotoxins may include a single type or a mixed type of R5.

Examples of the (C1-C30) alkoxy group include a straight-chain or branched (C1-C30) alkoxy group, and preferred is a straight-chain or branched (C1-C10) alkoxy group, including, for example, a methoxy group, an ethoxy group, an n-propoxy group, an i-propoxy group, an n-butoxy group, a t-butoxy group and the like. Examples of the (C7-C30)

aralkyloxy group include a straight-chain or branched (C7-C12) aralkyloxy group, and preferred is a straight-chain or branched (C1-C10) aralkyloxy group, including, for example, a 4-phenylbutoxy group and the like.

Examples of the (C1-C30) alkylamino group or di(C1-C30) alkylamino group include a straight-chain or branched (C1-C30) alkylamino group or a di(C1-C30) alkylamino group, and preferred is a straight-chain or branched (C1-C20) alkylamino group or a di(C1-C20) alkylamino group, including, for example, a methylamino group, an ethylamino group, an n-propylamino group, an i-propylamino group, an n-butylamino group, a t-butylamino group, a dimethylamino group, a diethylamino group, a di (n-butyl)amino group and the like.

Examples of the amino acid with a protected carboxyl group include an amino acid usually used in peptide synthesis, in which a carboxyl group is protected, including, for example, a phenylalanine benzyl ester and the like.

Examples of the group —N(R6)CONH(R7) [wherein R6 and R7, which may be identical or different, are a (C3-C6) cycloalkyl group or a (C1-C5) alkyl group optionally substituted with a tertiary amino group] include, but are not particularly limited to, for example, a cyclohexylaminocarbonylcyclohexylamino group, an isopropylaminocarbonylisopropylamino group, and the like.

Polyaspartic acid which is composed of two or more succinic acid monoamide moieties in the high-molecular weight conjugate of podophyllotoxins represented by the general formula (I) of the present invention, includes constituent units of α-amino acid type, β-amino acid type, cyclized type and the like. These constituent units are bound in any order, and may be bound to form a block-type form or a random-type form.

The total number of aspartic acid residues in the polyaspartic acid of the high-molecular weight conjugate of podophyllotoxins represented by the general formula (I) is represented by "d+e+f+g+h+i+j", and may be determined, for example, from the amount of the aspartic acid derivative used for the preparation of a block copolymer. The number of aspartic acid residues (d+e+f+g+h+i+j) is about 3 to 200, preferably about 6 to 100, particularly preferably 15 to 90.

The proportion of the number of aspartic acid residues bound to the podophyllotoxins (d+e) based on the total number of aspartic acid residues (d+e+f+g+h+i+j) is 1 to 100%, preferably 3 to 90%, more preferably 4 to 60%. Furthermore, the number of aspartic acid residues (d+e) is about 1 to 200, preferably about 1 to 100, particularly preferably about 1 to 90.

The number of aspartic acid residues to which the podophyllotoxins (d+e) are bound can be determined from, for example the amount of unreacted podophyllotoxins remaining in the reaction liquid after performing a dehydration condensation reaction for linking the podophyllotoxins via an ester bond in an organic solvent, as shown in the following Examples.

The proportion of the α-amino acid type (d+f+h) based on the total number of aspartic acid residues (d+e+f+g+h+i+j) is 10 to 100%, preferably 20 to 100%. The proportion of the β-amino acid type (e+g+i) is 0 to 90%, preferably 0 to 80%. The proportion can be appropriately changed, for example, by suitably selecting the deprotection conditions for the protecting group in the polyaspartic acid and the like.

In the general formula (I), t is an integer of from about 5 to 11,500, preferably an integer of from about 8 to 2,300, more preferably an integer of from about 100 to 300.

The high-molecular weight conjugate of podophyllotoxins of the present invention may form micelles with the polyethylene glycol moieties as the outer shell in water.

The high-molecular weight conjugate of podophyllotoxins of the present invention is obtained by ester-bonding a carboxylic acid group of a polymer having a polyethylene glycol moiety and two or more succinic acid monoamide moieties to a hydroxyl group of podophyllotoxins using a dehydrating condensing agent in an organic solvent, and the present invention also includes the manufacturing method; that is, a manufacturing method of subjecting, for example, a block copolymer of a polyethylene glycol moiety-polyaspartic acid produced by the method described in Patent Document 2, and podophyllotoxins in which the functional groups other than the group to be reacted are protected as necessary, to a reaction using a dehydrating condensing agent such as dicyclohexylcarbodiimide (DCC), diisopropylcarbodiimide (DIPC), 1-ethyl-3-(3-dimethylaminopropyl)carbodiimide hydrochloride (WSC) or 1-ethoxycarbonyl-2-ethoxy-1,2-dihydroxyquinolinone (EEDQ) at a temperature of 0 to 180° C., preferably at 5 to 50° C., in an organic solvent in which both of the substances are dissolved, preferably in an aprotic polar solvent such as N,N-dimethylformamide (DMF), 1,3-dimethyl-2-imidazolidin one (DMI) or N-methylpyrrolidone (NMP). Furthermore, a reaction aid such as N,N-dimethylaminopyridine (DMAP) may also be used in the condensation reaction. After condensation reaction, deprotection is performed as necessary, and conventional operations for separation and purification and the like are applied to obtain the high-molecular weight conjugate of the podophyllotoxins.

Furthermore, a high-molecular weight conjugate of podophyllotoxins in which R5 is a —N(R6)CONH(R7) group (wherein R6 and R7, which may be identical or different, are each a (C3-C6) cycloalkyl group or a (C1-C5) alkyl group optionally substituted with a tertiary amino group) may also be obtained by a reaction using the aforementioned carbodiimides as a condensing agent.

As a method of introducing as R5 a (C1-C30) alkoxy group, a (C7-C30) aralkyloxy group, a (C1-C30) alkylamino group, a di(C1-C30) alkylamino group or an amino acid with a protected carboxyl group into a compound of the general formula (I), there can be mentioned a method in which a carboxylic acid group of the polymer is first activated, and then reacted with a corresponding alcohol, a corresponding amine, or an amino acid with a protected carboxyl group and the like in an amount to be introduced under basic conditions; a method in which a corresponding alcohol, a corresponding amine, an amino acid with a protected carboxyl group and the like are first activated, and then reacted with a polymer; and the like. After the purification of the polymer, it is possible to re-activate any unreacted carboxylic acid groups in the polymer by the same reaction, and the re-activated carboxylic acid groups may be condensed with the hydroxyl group of podophyllotoxins. Alternatively, other alcohols, amines and the like may be repeatedly reacted to synthesize a mixture of polymers having various substituents as R5, to which podophyllotoxins may subsequently be condensed. Furthermore, after condensing the polymer with the podophyllotoxins, a (C1-C30) alkoxy group, a (C7-C30) aralkyloxy group, a (C1-C30) alkylamino group, a di(C1-C30) alkylamino group, an amino acid with a protected carboxyl group or the like may be introduced.

The method for manufacturing a high-molecular weight conjugate of podophyllotoxins of the present invention is not intended to be limited to the aforementioned methods.

The present invention also includes anticancer agents comprising the high-molecular weight conjugate of podophyllotoxins of the present invention as an active ingredient. The high-molecular weight conjugate can be used in a dosage form which is conventionally used, including, for example, injections, tablets, powders and the like. For formulation process, pharmaceutically acceptable carriers that are conventionally used, for example, binding agents, lubricants, disintegration agents, solvents, excipients, solubilizing agents, dispersants, stabilizing agents, suspending agents, preservatives, soothing agents, colorants, flavors and the like can be used. Among them, the use as an injection is preferred, and usually, for example, water, physiological saline, a 5% glucose or mannitol solution, water-soluble organic solvents (for example, glycerol, ethanol, dimethylsulfoxide, N-methylpyrrolidone, polyethylene glycol, cremophor and the like, and a mixture thereof), mixtures of water and water-soluble organic solvents, and the like are used.

The dosage of the high-molecular weight conjugate of podophyllotoxins of the present invention may can vary as a matter of course, depending on sex, age, physiological conditions, pathology and the like of patients, and the high-molecular weight conjugate is parenterally administered, typically at a does of 0.01 to 500 mg/m$^2$, preferably 0.1 to 250 mg/m$^2$, as an active ingredient per day for an adult. Administration by injection is performed intravenously, intraarterially, to the affected site (tumor site), or the like.

EXAMPLES

Hereinafter, the present invention will be illustrated more specifically with reference to Examples, but is not intended to be limited to these Examples.

Example 1

Synthesis of compound 1 (conjugate of etoposide and a block copolymer of a methoxypolyethylene glycol moiety having a molecular weight of 12,000 and a polyaspartic acid moiety having a polymerization number of 35: general formula (I) in which R1=Me (methyl group), R2=trimethylene group, R3=Ac (acetyl group), R4=etoposide residue, R5=isopropylaminocarbonyl-isopropylamino group, d+e+f+g+h+i+j=35, t=273)

A methoxypolyethylene glycol-polyaspartic acid block copolymer (polymerization number of aspartic acid: 35, 1.80 g) prepared according to the method described in Patent Document 3, and commercially available etoposide (700 mg) were dissolved in DMF (70 ml), and DMAP (72 mg) and DIPC (1.25 ml) were added thereto. The mixture was stirred for 20 hours at 25° C. To the reaction liquid, ethanol (105 ml), ethyl acetate (105 ml) and diisopropyl ether (840 ml) were added, and the mixture was stirred for 120 minutes at room temperature. Subsequently, the precipitate was collected by filtration, and washed with ethanol/diisopropyl ether (1/4 (v/v), 100 ml). The resultant precipitate was dissolved in acetonitrile/water (1/1 (v/v), 210 ml), and then the solution was passed through a column of an ion-exchange resin (Dowex 50 (H$^+$) manufactured by Dow Chemical Company, 15 ml), and eluted with acetonitrile/water (1/1 (v/v), 30 ml). After water (140 ml) was added to the eluted fraction thus obtained, acetonitrile was distilled off under reduced pressure, and then the residue was freeze-dried to obtain compound 1 (2.06 g).

On the basis of the amount of unreacted etoposide in the reaction liquid determined by HPLC (high performance liquid chromatography), the content of etoposide in compound 1 was determined as 16.5% (w/w), and the ratio of (d+e) based on (d+e+f+g+h+i+j) was determined as 15%. In compound 1, free etoposide was not detected.

According to this method, an isopropylaminocarbonyl-isopropylamino group can be added as R5, and the abundance ratio of the group was determined by $^1$H-NMR (hydrogen nuclear magnetic resonance spectrum) using compound 1 dissolved in sodium deuteroxide/deuterium oxide/deuterated acetonitrile. The ratio of the isopropylaminocarbonyl-isopropylamino group to the polyaspartic acid of compound 1, that is, the ratio of (f+g) based on (d+e+f+g+h+i+j) was 19.6%. The remaining aspartic acid residues are in the form of a free carboxylic acid (h+i) or a cyclic structure (j).

Example 2

Synthesis of compound 2 (conjugate of podophyllotoxin and a block copolymer of a methoxypolyethylene glycol moiety having a molecular weight of 12,000 and a polyaspartic acid moiety having a polymerization number of 35: general formula (I) in which R1=Me (methyl group), R2=trimethylene group, R3=Ac (acetyl group), R4=podophyllotoxin residue, R5=isopropylaminocarbonylisopropylamino group, d+e+f+g+h+i+j=35, t=273)

A methoxypolyethylene glycol-polyaspartic acid block copolymer (polymerization number of aspartic acid: 35, 226 mg) prepared according to the method described in Patent Document 3 and commercially available podophyllotoxin (106 mg) were dissolved in DMF (5 ml), and DMAP (12 mg) and DIPC (0.16 ml) were added thereto. The mixture was stirred for 20 hours at 25° C. To the reaction liquid, ethanol (15 ml) and diisopropyl ether (60 ml) were added, and the mixture was stirred for 120 minutes at room temperature. Then, the precipitate was collected by filtration, and washed with ethanol/diisopropyl ether (1/4 (v/v), 10 ml). The resultant precipitate was dissolved in acetonitrile/water (1/1 (v/v), 10 ml), and then the solution was passed through a column of an ion-exchange resin (Dowex 50 (H$^+$) manufactured by Dow Chemical Company, 2.5 ml), and eluted with acetonitrile/water (1/1 (v/v), 5 ml). After water (10 ml) was added to the eluted fraction thus obtained, acetonitrile was distilled off under reduced pressure. Subsequently, the residue was freeze-dried to obtain compound 2 (220 mg).

On the basis of the amount of unreacted podophyllotoxin in the reaction liquid was measured by HPLC (high performance liquid chromatography), the content of podophyllotoxin in compound 2 was determined as 10.6% (w/w), and the ratio of (d+e) based on (d+e+f+g+h+i+j) was determined as 13.1%. In compound 2, free podophyllotoxin was not detected.

According to this method, an isopropylaminocarbonyl-isopropylamino group can be added as R5, and the abundance ratio of the group was determined by $^1$H-NMR using compound 2 dissolved in sodium deuteroxide/deuterium oxide/deuterated acetonitrile The ratio of the isopropylaminocarbonylisopropylamino group to the polyaspartic acid of compound 2, that is, the ratio of (f+g) based on (d+e+f+g+h+i+j), was 15.2%. The remaining aspartic acid residues were in the form of free carboxylic acid (h+i) or a cyclic structure (j).

Example 3

Synthesis of compound 3 (conjugate of podophyllotoxin and a block copolymer of a methoxypolyethylene glycol moiety having a molecular weight of 12,000 and a polyaspartic acid moiety having a polymerization number of 33: general formula (I) in which R1 Me (methyl group), R2=trimethylene group, R3=Ac (acetyl group), R4=podophyllotoxin residue, R5=isopropylamino-carbonylisopropylamino group or O-benzyl-phenylalanyl group, d+e+f+g+h+i+j=33, t=273)

A methoxypolyethylene glycol-polyaspartic acid block copolymer (polymerization number of aspartic acid: 33, 464.4 mg) produced according to the method described in Patent Document 3, and commercially available podophyllotoxin (100 mg) were dissolved in DMF (6 ml), and DMAP (12 mg) and DIPC (0.09 ml) were added thereto. The mixture was stirred for 20 hours at 15° C. Subsequently, phenylalanine benzyl ester hydrochloride (36.8 mg), triethylamine (0.02 ml) and DIPC (0.23 ml) were added, and the mixture was stirred for 20 hours at 15° C., and then stirred for another 4 hours at 25° C. To the reaction liquid, ethylacetate (10 ml), ethanol (10 ml) and diisopropylether (80 ml) were added, and the mixture was stirred for 30 minutes at room temperature. Then, the precipitate was collected by filtration, and washed with ethanol/diisopropyl ether (1/4 (v/v), 20 ml). The resultant precipitate was dissolved in acetonitrile/water (1/1 (v/v), 20 ml), and then the solution was passed through a column of an ion-exchange resin (Dowex 50($H^+$) manufactured by Dow Chemical Company, 3 ml), and eluted with acetonitrile/water (1/1 (v/v), 20 ml). After water (25 ml) was added to the eluted fraction thus obtained, acetonitrile was distilled off under reduced pressure, and then the residue was freeze-dried to obtain compound 3 (580 mg).

On the basis of the amount of unreacted podophyllotoxin in the reaction liquid determined by HPLC (high performance liquid chromatography), the content of podophyllotoxin in compound 3 was determined as 13.7% (w/w), and the ratio of (d+e) based on (d+e+f+g+h+i+j) was determined as 19%. In compound 3, free podophyllotoxin was not detected.

The O-benzyl-phenylalanyl group introduced as one of R5 was determined by quantifying the amount of benzyl alcohol released by hydrolyzing compound 3 in acetonitrile-aqueous sodium hydroxide solution at 40° C. for 6 hours. The ratio of the O-benzyl-phenylalanyl group to the polyaspartic acid, that is, the ratio of the O-benzyl-phenylalanyl group bound to (f+g) based on (d+e+f+g+h+i+j), was 13%.

Furthermore, an isopropylaminocarbonylisopropylamino group can also be added as R5, and the abundance ratio of the group was determined by $^1$H-NMR (hydrogen nuclear magnetic resonance spectrum) using compound 3 dissolved in sodium deuteroxide/deuterium oxide/deuterated acetonitrile. The ratio of the isopropylaminocarbonylisopropylamino group to the polyaspartic acid, that is, the ratio of the isopropylaminocarbonylisopropylamino group bound to (f+g) based on (d+e+f+g+h+i+j) was 15%. As a result, the ratio of the total amount of R5 to the polyaspartic acid, that is, the ratio of (f+g) based on (d+e+f+g+h+i+j) was 28%. The remaining aspartic acid residues are in the form of a free carboxylic acid (h+i) or a cyclic structure (j).

Comparative Example 1

Synthesis of comparative compound 1 (conjugate of etoposide and a block copolymer of a methoxypolyethylene glycol moiety having a molecular weight of 12,000 and a polyglutamic acid moiety having a polymerization number of 23)

A methoxypolyethylene glycol-polyglutamic acid block copolymer (21 mg) prepared according to the method described in Japanese Patent Application Laid-Open (KO-KAI) No. 5-955, and commercially available etoposide (9.6 mg) were dissolved in DMF (1 ml), and DMAP (0.6 mg) and DIPC (0.01 ml) were added thereto. The mixture was stirred for 20 hours at 25° C. To the reaction liquid, ethanol (1.5 ml), ethyl acetate (1.5 ml) and diisopropyl ether (12 ml) were added, and the mixture was stirred for 30 minutes at room temperature. Then, a precipitate was collected by filtration, and washed with ethanol/diisopropyl ether (1/4 (v/v), 2 ml). The resultant precipitate was dissolved in acetonitrile/water (1/1 (v/v), 3 ml), and then the solution was passed through a column of an ion-exchange resin (Dowex 50 ($H^+$) manufactured by Dow Chemical Company, 0.2 ml), and eluted with acetonitrile/water (1/1 (v/v), 1 ml). After water (1 ml) was added to the eluted fraction thus obtained, and acetonitrile was distilled off under reduced pressure, and then the residue was freeze-dried to obtain comparative compound 1 (28.0 mg).

On the basis of the amount of unreacted etoposide in the reaction liquid determined by HPLC, the content of etoposide in comparative compound 1 was determined as 23.8% (w/w). In comparative compound 1, free etoposide was not detected.

Comparative Example 2

Synthesis of comparative compound 2 (conjugate of podophyllotoxin and a block copolymer of a methoxypolyethylene glycol moiety having a molecular weight of 12,000 and a polyglutamic acid moiety having a polymerization number of 23)

A methoxypolyethylene glycol-polyglutamic acid block copolymer (52 mg) produced according to the method described in Japanese Patent Application Laid-Open (KO-KAI) No. 5-955, and commercially available podophyllotoxin (10 mg) were dissolved in DMF (1 ml), and DMAP (2 mg) and DIPC (0.03 ml) were added thereto. The mixture was stirred for 20 hours at 25° C. To the reaction liquid, ethanol (3 ml) and diisopropyl ether (12 ml) were added, and the mixture was stirred for 30 minutes at room temperature. Then, the precipitate was collected by filtration, and washed with ethanol/diisopropyl ether (1/4 (v/v), 2 ml). The resultant precipitate was dissolved in acetonitrile/water (1/1 (v/v), 3 ml), and then the solution was passed through a column of an ion-exchange resin (Dowex 50 ($H^+$) manufactured by Dow Chemical Company, 0.2 ml), and eluted with acetonitrile/water (1/1 (v/v) 1 ml). After water (1 ml) was added to the eluted fraction thus obtained, acetonitrile was distilled off under reduced pressure. Subsequently, the residue was freeze-dried to obtain comparative compound 2 (64.3 mg).

On the basis of the amount of unreacted podophyllotoxin in the reaction liquid determined by HPLC, the content of podophyllotoxin in the comparative compound 2 was 16.0% (w/w). In comparative compound 2, free podophyllotoxin was not detected.

Test Example 1

Drug Release from Compound 1 in the Absence of Enzymes

Compound 1 or comparative compound 1 was dissolved in PBS (phosphate buffered physiological saline; pH 7.1) to a polymer concentration of 1 mg/ml, and the solution was incubated at 37° C. Etoposide released from the high-molecular weight conjugate was separated and quantified by HPLC in comparison with a standard curve. The proportion of the quantified value based on the total drug amount determined from the drug content in the high-molecular weight conjugate is shown in FIG. 1.

As is obvious from FIG. 1, the high-molecular weight conjugate of the present invention (compound 1) releases 85% or more of etoposide within 24 hours in the absence of hydrolyzing enzymes, whereas comparative compound 1 not having a succinic acid monoamide moiety virtually did not release etoposide in 24 hours. This result demonstrates the excellent drug release performance of the high-molecular weight conjugate of etoposide of the present invention in the absence of enzymes.

Test Example 2

Drug Release from Compounds 2 and 3 in the Absence of Enzymes

Compound 2 or 3 or comparative compound 2 was dissolved in PBS (phosphate buffered physiological saline; pH 7.1) to a polymer concentration of 1 mg/ml, and the solution was incubated at 37° C. Podophyllotoxin released from the high-molecular weight conjugate was separated and quantified by HPLC in comparison with a standard curve. The proportion of the quantified value based on the total drug amount determined from the drug content of the high-molecular weight conjugate is shown in FIG. 2.

As is obvious from FIG. 2, the high-molecular weight conjugate of the present invention (compound 2 or 3) released 10 to 60% or more of podophyllotoxin within 24 hours in the absence of hydrolyzing enzymes, where as comparative compound 2 not having a succinic acid monoamide moiety virtually did not release podophyllotoxin in 24 hours. This result demonstrates the excellent drug release performance of the high-molecular weight conjugate of podophyllotoxin of the present invention in the absence of enzymes. Furthermore, it is shown that the drug release performance can be freely controlled.

Test Example 3

Antitumor Effect of Compound 1

Mouse colon cancer, Colon 26, maintained by serial subcutaneous subculture in mice, was minced into about 2-mm square fragments, and the fragments were subcutaneously transplanted on the dorsal part of female CDF1 mice with a trocar. Seven days after tumor transplantation, the high-molecular weight conjugate of the present invention (compound 1) or the control drug (etoposide, ETP) was administered once intravenously to the mouse tail vein. The control group means a group to which the drug was not administered. Compound 1 was dissolved in a 5% glucose solution for injection and used. As for ETP, Rastet injection (manufactured by Nippon Kayaku Co., Ltd.) was diluted with a 5% glucose solution for injection and used. After the administration, the major axis (L mm) and the minor axis (W mm) of the tumor were measured using a caliper, and the tumor volume was calculated by the formula: $(L \times W^2)/2$. Table 1 shows the relative tumor volume based on the tumor volume on the day of administration. The changes of the body weight during this period of time is also shown in Table 1 as the relative body weight based on the body weight on the day of administration.

TABLE 1

|  |  | Days after administration | | |
|---|---|---|---|---|
|  |  | 0 | 4 | 8 |
| Compound 1 | Relative tumor volume | 1.00 | 0.86 | 1.69 |
| 450 mg/kg | Relative body weight | 1.00 | 0.87 | 0.97 |
| ETP | Relative tumor volume | 1.00 | 1.17 | 3.79 |
| 90 mg/kg | Relative body weight | 1.00 | 0.87 | 0.97 |
| Control | Relative tumor volume | 1.00 | 5.02 | 11.59 |
|  | Relative body weight | 1.00 | 0.98 | 0.82 |

Table 1 demonstrates that the high-molecular weight conjugate of the present invention has a superior anticancer activity over ETP at the dose (450 mg/kg) causing the body weight reduction to the same extent as that of ETP (90 mg/kg), and therefore can serve as an anticancer agent.

Test Example 4

Antitumor Action of Compounds 2 and 3

Mouse colon cancer, Colon 26, maintained by serial subcutaneous subculture in mice, was minced into about 2 mm-square fragments, and the fragments were transplanted subcutaneously on the dorsal part of female CDF1 mice with a trocar. Seven days after tumor transplantation (in Table 2, administration initiation day), the high-molecular weight conjugate of the present invention (compound 2 and compound 3) or a control drug (podophyllotoxin, POD) was administered intravenously to the mouse tail vein. Compound 2 and compound 3 were dissolved in a 5% glucose solution for injection and administered once. The control group means a group to which the drug was not administered. POD, purchased from Sigma-Aldrich Company, was diluted with dimethylsulfoxide and a 5% glucose solution for injection and administered for 5 consecutive days from the administration initiation day. After the administration, the major axis (L mm) and the minor axis (W mm) of the tumor were measured using a caliper, and the tumor volume was calculated by the formula: $(L \times W^2)/2$. Table 2 shows the relative tumor volume based on the tumor volume on the day of administration initiation. The changes of the body weight during this period of time is also shown in Table 2 as the relative body weight based on the body weight on the day of administration.

TABLE 2

|  |  | Days after administration initiation day | | | |
|---|---|---|---|---|---|
|  |  | 0 | 3 | 5 | 8 |
| Compound 2 75 mg/kg single administration | Relative tumor volume | 1.00 | 0.82 | 0.80 | 2.24 |
|  | Relative body weight | 1.00 | 0.96 | 0.99 | 1.00 |
| Compound 3 75 mg/kg single administration | Relative tumor volume | 1.00 | 1.79 | 2.05 | 3.26 |
|  | Relative body weight | 1.00 | 0.95 | 0.98 | 0.94 |
| POD 15 mg/kg administered for 5 consecutive days (total 75 mg/kg) | Relative tumor volume | 1.00 | 1.58 | 1.79 | 6.08 |
|  | Relative body weight | 1.00 | 1.01 | 0.96 | 0.98 |
| Control | Relative tumor volume | 1.00 | 3.01 | 4.38 | 6.52 |
|  | Relative body weight | 1.00 | 0.99 | 0.97 | 0.86 |

Table 2 demonstrates that the high-molecular weight conjugates of the present invention have a superior anticancer activity over POD at an amount of administration (75 mg/kg) with which the body weight reduction occurs to the same extent as that of POD (15 mg/kg/day, administered for 5 consecutive days), in spite of a single administration, and therefore can serve as an anticancer agent.

BRIEF DESCRIPTION OF DRAWINGS

In FIG. 1, -●- represents the percentage of the amount released from compound 1 of the present invention, and -○- represents the percentage of the amount released from comparative compound 1.

In FIG. 2, -♦- represents the percentage of the amount released from compound 2 of the present invention, -▲- represents the percentage of the amount released from compound 3, and -◇- represents the percentage of the amount released from comparative compound 2.

Figure 1:
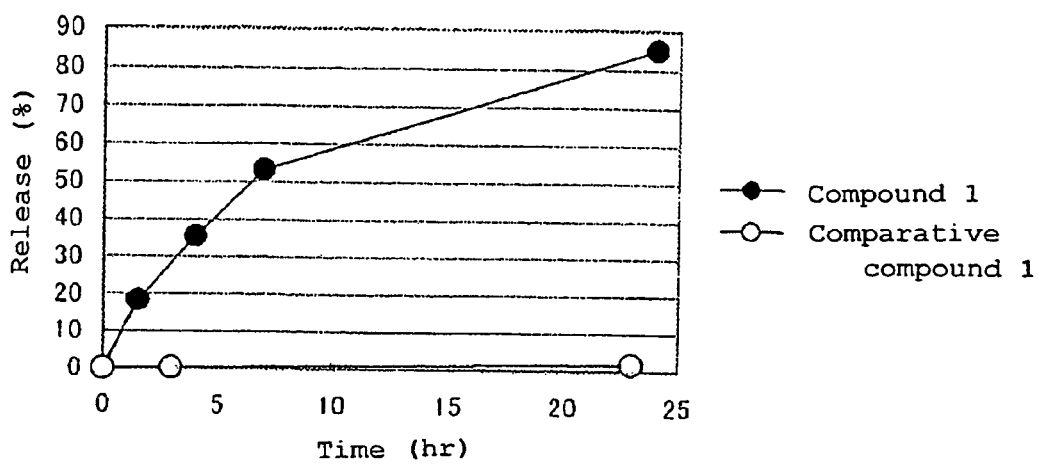
FIG. 1 shows the percentage of the amount of etoposide released from compound 1 (high-molecular weight derivative in which etoposide is bound to polyaspartic acid of the block copolymer) or comparative compound 1 (high-molecular weight derivative in which etoposide is bound to polyglutamic acid of the block copolymer) in PBS solutions (pH 7.1, 37° C.), based on the total amount of bound etoposide.
Figure 2:
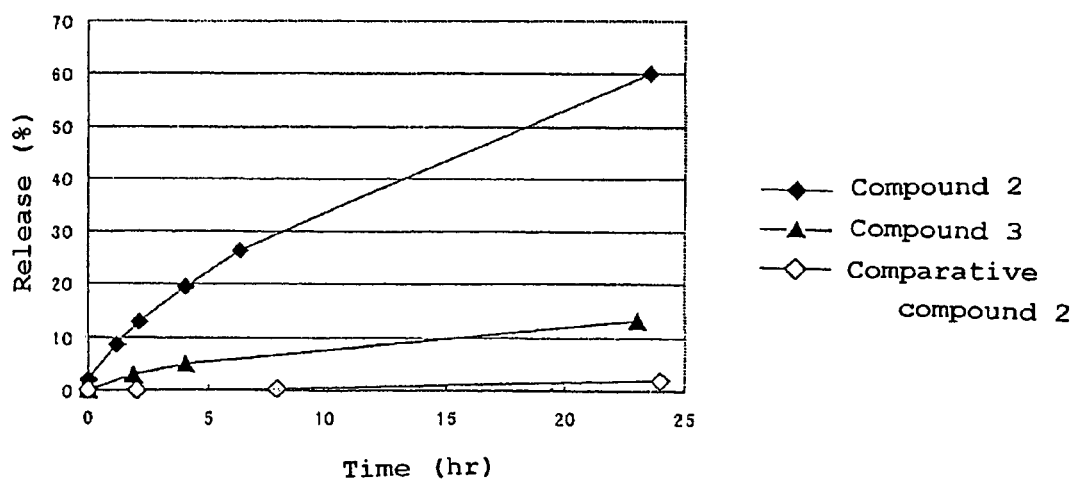
FIG. 2 shows the percentage of the amount of podophyllotoxin released from compound 2 or compound 3 of the present invention (high-molecular weight derivatives in which podophyllotoxin is bound to polyaspartic acid of the block copolymer) or comparative compound 2 (high-molecular weight derivative in which podophyllotoxin is bound to polyglutamic acid of the block copolymer) in PBS solutions (pH 7.1, 37° C.), based on the total binding amount of podophyllotoxin.

The invention claimed is:

1. A high-molecular weight conjugate of podophyllotoxins, represented by formula (I):

$$R_1-O-(CH_2CH_2O)_t-R_2-[(NHCOCH)_d-$$
$$|$$
$$CH_2CO_2R_4$$

$$CO_2R_4 \qquad\qquad COR_5$$
$$| \qquad\qquad |$$
$$-(NHCOCH_2CH)_e-(NHCOCH)_f-(NHCOCH_2CH)_g-$$
$$|$$
$$CH_2COR_5$$

$$CO_2H$$
$$|$$
$$-(NHCOCH)_h-(NHCOCH_2CH)_i-(NCOCH)_j]-NHR_3$$
$$| \qquad\qquad |\ /$$
$$CH_2CO_2H \qquad\qquad COCH_2$$

wherein R1 represents a hydrogen atom or a (C1-C6) alkyl group; R2 represents a linking group; R3 represents a hydrogen atom or a (C1-C6) acyl group; R4 represents the residue of a hydroxyl group of the podophyllotoxins; R5 represents a group selected from the group consisting of a (C1-C30) alkoxy group, a (C7-C30) aralkyloxy group, a (C1-C30) alkylamino group, a di(C1-C30) alkylamino group, an amino acid with a protected carboxyl group, and —N(R6)CONH(R7) wherein R6 and R7, which may be identical or different, each represent a (C3-C6) cyclic alkyl group or a (C1- C5) alkyl group optionally substituted with a tertiary amino group; t represents an integer from 5 to 11,500; d, e, f, g, h, i and j each independently represent an integer from 0 to 200, provided that d+e represents an integer from 1 to 200, and d+e+f+g+h+i+j represents an integer from 3 to 200, and that the respective constituent units of polyaspartic acid are bound in any order.

2. The high-molecular weight conjugate of podophyllotoxins according to claim 1, wherein R1 is a (C1-C6) alkyl group; R2 is a (C2-C6) alkylene group; R3 is a (C1-C6) acyl group; t is an integer from 8 to 2300; and d, e, f, g, h, i and j are each independently an integer from 0 to 100, provided that d+e is an integer from 1 to 100, and d+e+f+g+h+i+j is an integer from 6 to 100.

3. The high-molecular weight conjugate of podophyllotoxins according to claim 2, wherein R1 is a (C1-C3) alkyl group; R2 is (C2-C4) alkylene group; R3 is a (C1-C3) acyl group; t is an integer from 100 to 300; and d, e, f, g, h, i and j are each independently an integer from 0 to 90, provided that d+e is an integer from 1 to 90, and d+e+f+g+h+i+j is an integer from 15 to 90.

4. The high-molecular weight conjugate of podophyllotoxins according to any one of claims 1 to 3, wherein the podophyllotoxins are podophyllotoxin, etoposide or teniposide.

5. A high-molecular weight conjugate of podophyllotoxins, obtained by ester-bonding a carboxylic acid group of a polymer having a polyethylene glycol moiety and two or more succinic acid monoamide moieties to a hydroxyl group of the podophyllotoxins using a dehydrating condensing agent in an organic solvent.

* * * * *